(12) United States Patent
De Backer et al.

(10) Patent No.: US 7,659,391 B2
(45) Date of Patent: Feb. 9, 2010

(54) METHOD FOR THE IN VITRO SYNTHESIS OF SHORT DOUBLE STRANDED RNAS

(75) Inventors: Marianne Denise De Backer, Beerse (BE); Adam N. Harris, Oceanside, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 392 days.

(21) Appl. No.: 10/494,663

(22) PCT Filed: Oct. 30, 2002

(86) PCT No.: PCT/EP02/12165

§ 371 (c)(1),
(2), (4) Date: May 4, 2004

(87) PCT Pub. No.: WO03/040294

PCT Pub. Date: May 15, 2003

(65) Prior Publication Data

US 2004/0259097 A1  Dec. 23, 2004

Related U.S. Application Data

(60) Provisional application No. 60/337,975, filed on Nov. 5, 2001.

(51) Int. Cl.
*C07H 21/00* (2006.01)
(52) U.S. Cl. .................................................. 536/25.3
(58) Field of Classification Search ................. 536/25.3
See application file for complete search history.

(56) References Cited

U.S. PATENT DOCUMENTS

| 5,614,403 | A  | * | 3/1997  | Ramig et al. | ............ | 435/235.1 |
| 6,214,546 | B1 | * | 4/2001  | Asher et al. | ............ | 435/6 |
| 6,506,559 | B1 | * | 1/2003  | Fire et al.  | ............ | 435/6 |
| 6,958,217 | B2 | * | 10/2005 | Pedersen     | ............ | 435/6 |
| 7,282,564 | B2 | * | 10/2007 | Mello et al. | ............ | 530/350 |
| 2003/0166282 | A1 | * | 9/2003 | Brown et al. | ............ | 435/455 |

FOREIGN PATENT DOCUMENTS

| WO | WO 00/63364    |    | 10/2000 |
| WO | WO 01/75164 A2 |    | 10/2001 |
| WO | WO 01/75164 A3 |    | 10/2001 |

OTHER PUBLICATIONS

Yu Jenn-Yan et al., "RNA interference by expression of short-interfering RNAs and hairpin RNAs in mammalian cells", Proceedings of the National Academy of Sciences of the United States, vol. 99, No. 9, pp. 6047-6052 (2002).
Livache et al., "Detection of HIV, DNA in Biological Samples by an Homogenous Assay: Fluorescence Measurement of Double-Stranded RNA Synthesized from Amplified DNA", Analytical Biochemistry, vol. 217, No. 2, pp. 248-254 (1994).
Goto Akira et al., α-, β-, or γ-chain-specific RNA interference of laminin assembly in *Drosophila* Kc167 cells, Biochemical Journal, vol. 360, No. 1, pp. 167-172 (2001).
Elbashir et al., "Duplexes of 21-nucleotide RNAs mediate RNA interference in cultured mammalian cells", Nature, vol. 411, No. 6836. 3, pp. 494-498 (2001).
Milligan et al., "Oligoribonucleotide synthesis using T7 RNA polymerase and synthetic DNA templates", Nucleic Acids Research, vol. 15, No. 21, pp. 8783-8798 (1987).
Hayes et al., "Complete replication of a satellite RNA in vitro by a purified RNA-dependent RNA polymerase", Journal of General Virology, vol. 73, No. 6, pp. 1597-1600 ((1992).

* cited by examiner

*Primary Examiner*—Brian Whiteman

(57) ABSTRACT

The present invention relates to the field of synthesis of short double-stranded RNAs. An in vitro transcription method using bacteriophage polymerases and target sequence-specific single-stranded DNA oligonucleotides as templates is disclosed. The present invention finds particularly advantageous use in the synthesis of short interfering RNAs (siRNAs) that have been shown to function as key intermediates in triggering sequence-specific RNA degradation during post-transcriptional gene silencing in plants and RNA interference in invertebrates and vertebrate systems.

3 Claims, 5 Drawing Sheets

Fig. 1

Target: 19nt within the coding sequence of the JNK2α1 mRNA

5'...ggaucaugaaagaaugucc...

Desired siRNA composition:

sense      5'    ggaucaugaaagaauguccuu antisense  3'  uuccuaguacuuucuuacagg

Hybridized DNA oligonucleotide templates for T7 RNA polymerase transcription:

For sense:    5' TAATACGACTCACTATAgg
                     3' ATTATGCTGAGTGATATCctagtactttcttacaggaa
                     T7 promoter sequence For antisense: 5' TAATACGACTCACTATAgg
                     3' ATTATGCTGAGTGATATCctgtaagaaagtactaggaa
                     T7 promoter sequence GL3 siRNA 1:     5'     ggcuaugaagagauacgccuu
                 3' uuccgauacuucucuaugcgg GL3 siRNA 2:     5'     gggcauuucgcagccuaccuu
                 3'  uucccguaaagcgucggaugg GL3 siRNA 3:     5'     ggugccaacccuauucuccuu
                 3'  uuccacgguugggauaagagg GL3 siRNA oligo: 5'     cuuacgcugaguacuucgaTT
                 3'  TTgaaugcgacucaugaagcu EGFP ds siRNA 2:        5'    gggcgaggagcuguucaccuu
                        3'    uucccgcuccucgacaagugg EGFP ds siRNA oligo:    5'    ccaccggcaagcugcccguTT
                        3'    TTgguggccguucgacgggca

Fig. 4A 1.  5'    ggaucaugaaagaauguccuu
    3' uuccuaguacuuucuuacagg 2.  5'    gguguuguaaaagaucagccuu
    3' uuccacaacauuuucuagucgg Oligo.  5'    ccaagggauuguuugugcuTT
        3' TTgguucccuaacaaacacga

Fig. 4B 1.  5' ggcagcguuacccaguccuu
    3' uuccgucgcaaugggucaggg 2.  5' ggcuccuccucacaguccuu
    3' uuccgaggaggagugucaggg 3.  5' ggagccuaccccugcccccuu
    3' uuccucggauggggacggggg 4.  5' ggaaaggaaaacgccguccuu
    3' uuccuuuccuuuugcggcagg

METHOD FOR THE IN VITRO SYNTHESIS OF SHORT DOUBLE STRANDED RNAS

CROSS REFERENCE TO RELATED APPLICATIONS

This application claims priority from PCT/EP02/12165, filed on Oct. 30, 2002, which claims priority from a Provisional Patent application No. 60/337,975, filed on Nov. 5, 2001. The complete disclosures of the above-identified applications are incorporated herein by reference in their entirety.

The present invention relates to the field of synthesis of short double-stranded target-specific RNAs. An in vitro transcription method using RNA polymerases and target sequence-specific DNA oligonucleotides as templates is disclosed. The present invention finds particularly advantageous use in the synthesis of short interfering RNAs (siRNAs) that have been shown to function as key intermediates in triggering sequence-specific RNA degradation during posttranscriptional gene silencing in plants and RNA interference in invertebrates and vertebrate systems.

BACKGROUND OF THE INVENTION

RNA silencing is a remarkable type of gene regulation based on sequence-specific targeting and degradation of RNA. RNA silencing was first discovered in transgenic plants, where it was termed cosuppression or posttranscriptional gene silencing (PTGS). Only recently a sequence-specific RNA degradation process, RNA interference (RNAi), related to PTGS has been found in ciliates, fungi and a variety of animals from C. elegans to mice and human cells. Although they may differ in detail, RNAi and PTGS result from the same highly conserved mechanism, indicating an ancient origin. The basic process involves a double stranded RNA (dsRNA) that is cleaved into small double stranded interfering RNAs (siRNA) which guide recognition and targeted cleavage of homologous mRNA. These small dsRNAs resemble breakdown products of an RNase III-like digestion. In particular, siRNAs are target-specific short double stranded RNAs wherein each strand of the siRNAs carries 5'monophosphate, 3'hydroxyl termini and 3' overhangs of 2-3 nucleotides (Caplen, N. et al., 2001, PNAS (98) 9742-9747).

RNAi has attracted considerable attention because it is a means of knocking out the activity of specific genes, being particularly useful in species that were previously considered not to be amendable to genetic analysis. Recent studies demonstrated that synthetic siRNAs can induce gene-specific inhibition of expression in C. elegans and in cell lines from humans and mice (Caplen N., et al., 2001, PNAS (98) 9742-9747; Elbashir S., et al., 2001, Nature (411) 494-498). In said publications it was further demonstrated that in mammalian cells siRNAs provide a sequence specific answer compared to the use of longer dsRNAs which inactivate the translation factor eIF2α, leading to a generalized suppression of protein synthesis. Also, in comparison to inhibition of gene expression using antisense technology, siRNAs seem to be very stable and thus may not require the extensive chemical modifications that single stranded RNA antisense oligonucleotides require to enhance the in vivo half life.

It is therefore to be expected that RNA silencing using siRNAs will become an important tool in engineering control of gene expression as well as in functional genomics and a variety of biotechnology applications ranging from molecular farming to possibly even gene therapy in animals. As different siRNAs may work with different effectiveness on their targets, the testing of more than one siRNA for a particular target will be desirable. In addition, genome-scale reverse genetics programs will require large numbers of siRNAs.

However, production of double stranded target-specific RNA oligos by traditional chemical synthesis remains relatively slow and expensive when compared to DNA oligo synthesis. In addition, chemical synthesis of RNA oligos requires special synthesizers and complex purification protocols. The present invention provides an alternative approach to produce short double stranded target-specific RNAs based on in vitro transcription using bacteriophage or other viral polymerases and target sequence-specific oligonucleotide templates. Compared to the chemical synthesis of RNA oligos the present invention is relatively quick and easy to perform.

However, the in vitro transcribed siRNAs differ from the chemically synthesized RNA oligos in two ways. Primarily, identical to the natural occurring siRNAs, the chemically synthesized RNA oligos have a 5'monophosphate group. The in vitro transcribed siRNAs retain a 5'triphosphate group. It was unknown whether the presence of this triphosphate group renders the in vitro transcribed siRNAs incompetent to induce RNA interference.

Secondly, chemically synthesized RNA oligos are highly purified using amongst others Ion Exchange and Reverse Phase HPLC wherein purity and quality of the synthesized compounds is further evaluated using amongst others NMR and mass spectrometry analysis. In the present invention a simple, crude purification protocol is used comprising size exclusion chromatography, phenol:chloroform extraction and ethanol precipitation. It was again uncertain whether the ommitance of an extensive purification protocol would affect the usefulness of "in vitro" transcribed RNAs in RNA-mediated silencing.

Surprisingly, the present invention demonstrates that the 5'triphosphate group and the crude purification does not affect the RNA silencing activity of "in vitro" transcribed RNAs and provides an alternative approach to siRNA synthesis which makes it accessible as a research tool in an average molecular biology laboratory.

Existing in vitro methods to synthesize small single stranded RNAs of defined length and sequence (Milligan F. et al., 1987, Nucleic Acid Res. (15) 8783-8798), were not directly applicable for the synthesis of small interfering RNAs. The problem resides in the fact that RNA polymerases tend to transcribe some nucleotides from the promoter sequence into the transcript. As a consequence, the target-specific dsRNAs which can be produced by annealing complementary single stranded RNA molecules generated using the aforementioned methods, must comprise at the 5'end the nucleotides transcribed from the promoter sequence and at the 3'end the nucleotides complementary to the nucleotides transcribed from the promoter sequence. It may well be that in the mRNA of the target sequence no stretch of a defined sequence length exists wherein the 5'-end consists of the nucleotides transcribed from the promoter sequence and the 3'-end of the nucleotides complementary to the nucleotides transcribed from the promoter sequence. The present invention solves this problem by providing truncated RNA polymerase promoter sequences wherein one or more nucleotides at the 5'end of the template strand of the promoter sequence are replaced by nucleotides that are part of the target-specific sequence. These substitutions do not affect the in vitro transcription yields, but increase the possibility that at least one target-specific sequence of a defined sequence length exists in the mRNA of the target protein, wherein the 5'-end consists of the nucleotides transcribed from the promoter sequence and the 3'-end of the nucleotides complementary to the nucleotides transcribed from the promoter sequence.

This and other aspects of the invention will be described herein below.

SUMMARY OF THE INVENTION

The present invention provides an in vitro method for the synthesis of short double stranded target-specific RNAs comprising the steps of a) combining a sense target-specific oligonucleotide template and a chain extending enzyme in a reaction mixture such that the template extended sense oligoribonucleotide product is formed; b) combining an antisense target-specific oligonucleotide template and a chain extending enzyme in a reaction mixture such that the template extended antisense oligoribonucleotide product is formed; and c) hybridizing the sense oligoribonucleotide product obtained in step a) with the complementary antisense oligoribonucleotide product obtained in step b).

In a further embodiment of the present invention the chain extending enzyme is an RNA polymerase and the oligonucleotide templates of step a) and b) comprise an RNA polymerase promoter sequence, preferably consisting of dsDNA. In a more preferred embodiment the RNA polymerase is T7 polymerase and the oligonucleotide templates of step a) and b) comprise a T7 RNA polymerase promoter sequence extended at the 5'end of the template strand with the target-specific template sequence, optionally extended with 2 or 3 additional nucleotides. The present invention finds particular use in the synthesis of small interfering RNAs. It is therefore, a further objective of the present invention to provide a method for the synthesis of target-specific short double stranded RNAs, wherein said target-specific short double stranded RNAs are less than 50 nucleotides, preferably less than 30 nucleotides long, even more preferably 30-12 nucleotides long, further characterised by comprising at the 5'-end nucleotides transcribed from the promoter sequence and at the 3'-end nucleotides complementary to the nucleotides transcribed from the promoter sequence.

Accordingly, the present invention provides a method for the synthesis of small interfering RNAs comprising the steps of a) combining a sense siRNA template with a chain extending enzyme in a reaction mixture such that the template extended sense oligoribonucleotide product is formed; b) combining an antisense siRNA template with a chain extending enzyme in a reaction mixture such that the template extended antisense oligoribonucleotide product is formed; and c) hybridizing the sense oligoribonucleotide product obtained in step a) with the antisense oligoribonucleotide product obtained in step b); wherein the siRNA templates of step a) and b) comprise a double stranded RNA polymerase promoter sequence extended at the 5'end of the template strand with the target-specific template sequence and 2 or 3 additional nucleotides. In a preferred embodiment the chain extending enzyme is T7 RNA polymerase and the siRNA templates comprise a double stranded T7 RNA polymerase promoter sequence, preferably the truncated T7 RNA polymerase promoter sequence shown in FIG. 1.

It is a further object of the present invention to provide kits to perform the methods according to the invention as well as the compounds for use in any of the methods disclosed.

BRIEF DESCRIPTION OF THE DRAWING

FIG. 1: Oligonucleotide production scheme. An example is given for the design of siRNA oligonucleotide templates for a target sequence of 19 nucleotides within the coding sequence of JNK2α1 mRNA. Figure discloses SEQ ID NOS: 1, 19-20 and 2-5, respectively, in order of appearance. The T7 promoter sequence is disclosed as SEQ ID NO: 56.

FIG. 4A: JNK2α1 target-specific double stranded siRNAs used in JNK2α1 transfected HeLa cells. Figure discloses SEQ ID NOS: 33-38, respectively, in order of appearance.

FIG. 4B: CDS-1 target-specific double stranded siRNAs used in CDS-1 transfected HeLa cells. Figure discloses SEQ ID NOS: 39-46, respectively, in order of appearance.

DETAILED DESCRIPTION

Figures 2A, 2B:
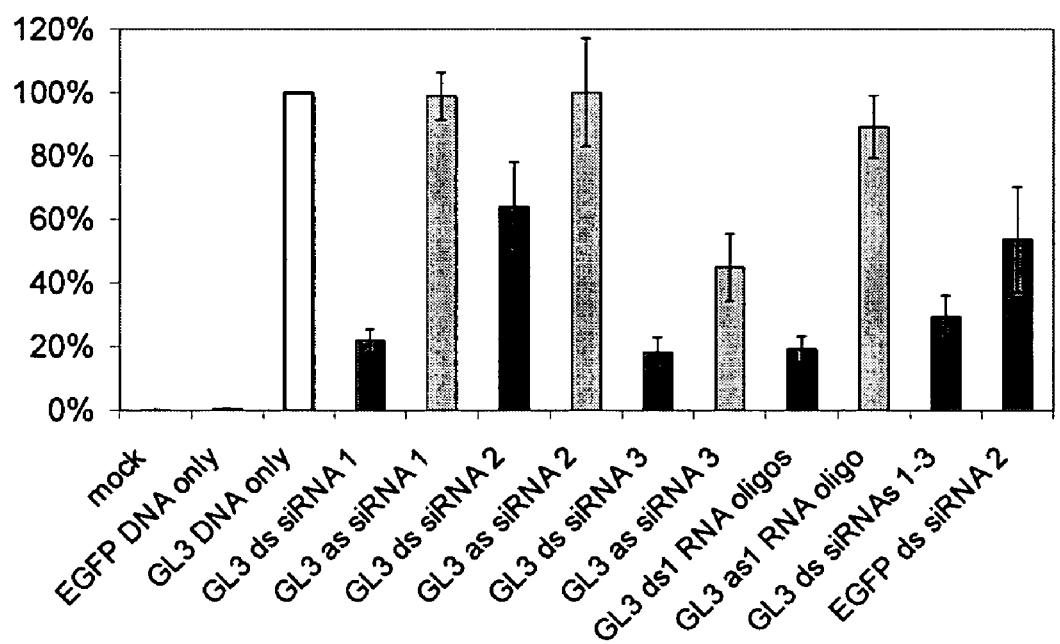
FIG. 2A: GL3 target-specific double stranded siRNAs used in a luciferase reporter assay. GL3 siRNA 1, GL3 siRNA 2 and GL3 siRNA 3 were made using the in vitro method of the invention. GL3 siRNA oligo was chemically synthesized (Vargeese, C. et al., 1988, Nucleic Acid Res. (26), 1046-1050) Figure discloses SEQ ID NOS: 21-28, respectively, in order of appearance.
FIG. 2B: Effects of GL3 target-specific siRNAs and of GL3 antisense single stranded siRNAs on luciferase expression in HeLa cells. Cells transfected with GL3-control luciferase+reporter constructs were taken as 100%.

This invention relates to the field of synthesis of short double-stranded target-specific RNAs and is based on the in vitro transcription of oligonucleotide templates using chain extending enzymes.

Target-specific short double stranded RNAs as used herein refers to a double-stranded RNA that matches part of the sequence encoding for a specific protein, i.e. the target protein. These sequences are preferably less than 50 nucleotides, more preferably less than 30 nucleotides long, even more preferably 15-25 nucleotides long. In a particular embodiment the target-specific short double stranded RNAs are useful in RNA interference in invertebrate and invertebrate systems as small interfering RNAs (siRNAs). siRNAs as used herein are short dsRNA molecules of 12-30 nucleotides, with 2- or 3-nucleotide overhanging 3'-ends. In a preferred embodiment the siRNAs are 15-25 nucleotides long with 2 nucleotide overhanging 3'ends. Even more preferred the siRNAs are 17-22 nucleotides long with 2 nucleotide overhanging 3'ends.

In order to obtain dsRNA both a sense and an antisense oligonucleotide template are required. The term "oligonucleotide templates" as used herein refers to structures that in some direct physical process can cause the patterning of a second structure, usually complementary to it in some sense. In current biology almost exclusively used to refer to a nucleotide sequence that directs the synthesis of a sequence complementary to it by the rules of Watson-Crick base-pairing (The Dictionary of Cell and Molecular Biology, 3d. Edition, Academic Press, London, 1999 (ISBN 0-12-432565-3)). These template sequences are preferably less than 50 nucleotides long, and may either be double stranded, single stranded or partially single stranded DNA oligo templates.

The oligonucleotide templates could either be synthetic DNA templates or templates generated as linearized plasmid DNA from a target-specific sequence cloned into a restriction site of a vector such as for example a prokaryotic cloning vector (pUC13, pUC19) or PCR cloning systems such as the TOPO cloning system of Invitrogen. The synthetic DNA templates may be produced according to techniques well known in the art. In a preferred embodiment of the present invention the oligonucleotide templates consist of partially single-stranded DNA oligo templates comprising an RNA polymerase promoter sequence consisting of dsDNA. In this embodiment the target-specific short double stranded RNAs are further characterized by comprising at the 5'end nucleotides transcribed from the RNA polymerase promoter sequence and at the 3'end nucleotides complementary to the nucleotides transcribed from the promoter sequence.

A "Chain extending enzyme" as defined herein refers to an enzyme capable of forming an RNA polymer from ribonucleoside 5'triphosphates; the RNA formed is complementary to the DNA template. The enzyme adds mononucleotide units to the 3'-hydroxyl ends of the RNA chain and thus builds RNA in the 5'–>3' direction, antiparallel to the DNA strand used as template. Such chain extending enzymes could for example be DNA dependent polymerases such as DNA polymerase I, II and III; RNA-directed DNA polymerases such as RSV and AMV-polymerases; DNA-directed RNA polymerases such as E.coli RNA polymerase; RNA-directed RNA polymerases such as the bacteriophage RNA polymerases, also known as RNA replicases; or the bacterial polynucleotide phosphorylases.

In a preferred embodiment the chain extending enzyme is an RNA polymerase. Said RNA polymerases require the presence of a specific initiation site within the DNA template. This initiation site, herein after referred to as "RNA polymerase promoter sequence", is the site where the RNA polymerase binds to the DNA template. It is also the site recognized by the RNA polymerase as an initiation signal, to indicate where transcription to form RNA begins.

Accordingly, the present invention provides oligonucleotide templates comprising an RNA polymerase promoter sequence consisting of dsDNA wherein the polymerase promoter sequence is recognized by an RNA polymerase. The term "recognized" as used herein intends to include all truncated RNA polymerase promoter sequences shortened by one or more nucleotides at one or either side of the promoter sequence with no or little effect on the binding of the RNA polymerase to the initiation site and with no or little effect on the transcription reaction. For example, Milligan et al. (Milligan F. et al., 1987, Nature (15) 8783-8798) demonstrated for the T7 RNA polymerase that its promoter does not appear to require the DNA in the non-template strand in the region −17 to −14 and −3 to +6, since removing these nucleotides has little effect on the transcription reaction. Also, truncation of the template strand beyond position +2, i.e. positions +3 to +6, has little effect on the yield of the reaction (Milligan F. et al., 1987, Nature (15) 8783-8798). The thus obtained truncated RNA polymerase promoter sequences are meant to be included as "RNA polymerase promoter sequences recognized by said RNA polymerase". Thus, in a specific embodiment of the present invention the RNA polymerase promoter sequence consists of the truncated RNA polymerase promoter sequence wherein one or more nucleotides are deleted at one or either side of the template strand of the promoter sequence. Preferably, the truncated RNA polymerase promoter consists of the T7 RNA polymerase promoter sequence truncated at positions +3 to +6 at the 5'end of the template strand as shown in FIG. 1.

Accordingly, it is a first object of the present invention to provide a method for the synthesis of short double stranded target-specific RNAs. The method comprising the steps of a) combining a target-specific sense oligonucleotide template and a chain extending enzyme in a reaction mixture such that the template extended sense oligoribonucleotide product is formed; b) combining a target-specific antisense oligonucleotide template and a chain extending enzyme in a reaction mixture such that the template extended antisense oligoribonucleotide product is formed; c) hybridizing the sense oligoribonucleotide product obtained in step a) with the antisense oligoribonucleotide product obtained in step b).

The chain-extending enzyme according to the method of the invention is preferably an RNA polymerase selected from the group consisting of T7 RNA polymerase, T3 RNA polymerase and SP6 RNA polymerase. In a more preferred embodiment the RNA polymerase consists of T7 RNA polymerase.

Accordingly, the oligonucleotide templates used in a method according to the invention, comprise an RNA polymerase promoter sequence consisting of dsDNA, wherein the RNA polymerase promoter sequence is recognized by an RNA polymerase selected from the group consisting of T7 RNA polymerase, T3 RNA polymerase and SP6 RNA polymerase. In a preferred embodiment the RNA polymerase promoter sequence is recognized by T7 RNA polymerase. In a more preferred embodiment the T7 RNA polymerase promoter sequence consists of the truncated T7 RNA polymerase promoter sequence as shown in FIG. 1.

In a further embodiment, the oligonucleotide templates used in a method according to the invention are characterized by being partially double stranded DNA oligo templates comprising a double stranded RNA polymerase promoter sequence which is extended at the 5'end of the template strand with the target-specific template sequence, optionally extended with 2 or 3 additional nucleotides. In a more preferred embodiment the target-specific template sequence comprises at the 5'end nucleotides transcribed from the promoter sequence and at the 3'end nucleotides complementary to the nucleotides from the promoter sequence. In the specific embodiment where the oligonucleotide templates comprise the truncated T7 RNA polymerase promoter sequence shown if FIG. 1, the target-specific template sequence comprises at the 5'end two guanosine (g) nucleotides and at the 3'end two cytosine (c) nucleotides.

Accordingly, it is a second embodiment of the present invention to provide a method for the synthesis of small interfering RNAs (siRNAs) comprising the steps of a) combining a sense siRNA template with a chain extending enzyme in a reaction mixture such that the template extended sense oligoribonucleotide product is formed; b) combining an antisense siRNA template with a chain extending enzyme in a reaction mixture such that the template extended antisense oligoribonucleotide product is formed; and c) hybridizing the sense oligoribonucleotide product obtained in step a) with the antisense oligoribonucleotide product obtained in step b); whereby the siRNA templates of step a) and b) comprise a double stranded RNA polymerase promoter sequence extended at the 5'-end of the template strand with the target-specific template sequence and 2 or 3 additional nucleotides. In a preferred embodiment the chain-extending enzyme used in the synthesis of siRNAs consists of an RNA polymerase, preferably selected from T7 RNA polymerase, T3 RNA polymerase or SP6 RNA polymerase. Accordingly the siRNA templates used in the method according to the invention comprise an RNA polymerase promoter sequence, which is recognized by an RNA polymerase, selected from the group consisting of T7 RNA polymerase, T3 RNA polymerase and SP6 RNA polymerase. In a more preferred embodiment the chain-extending enzyme is T7 RNA polymerase. Accordingly, in a preferred embodiment the RNA polymerase promoter sequence of the siRNA templates is recognized by T7 RNA polymerase. In a further embodiment the siRNA template comprises the double stranded truncated T7 RNA polymerase promoter sequence as shown in FIG. 1, wherein said truncated T7 RNA polymerase promoter sequence is extended at the 5'end of the template strand according to the method of the invention and wherein the target-specific template sequence comprises at the 5'end the nucleotides transcribed from the promoter sequence and at the 3'end nucleotides complementary to the nucleotides transcribed from the promoter sequence. In a specific embodiment the siRNA templates used in a method of the invention, comprise the double stranded truncated T7 RNA polymerase promoter sequence as shown in FIG. 1, wherein said truncated T7 RNA polymerase promoter sequence is extended at the 5'end of the template strand according to the method of the invention and wherein the target-specific template sequence comprises at the 5'end two guanosine (g) nucleotides and at the 3'end two cytosine (c) nucleotides.

The reaction conditions in either of the aforementioned methods to obtain a template extended oligoribonucleotide product are generally known in the art. In essence, the starting materials for enzymatic transcription to produce RNA are a DNA template, an RNA polymerase enzyme and the nucleoside triphosphates (NTPs) for the four required ribonucleotide bases, adenine, cytosine, guanine and uracyl, in a reaction buffer optimal for the RNA polymerase enzyme activity. For example, the reaction mixture for an in vitro transcription using T7 RNA polymerase typically contains, T7 RNA polymerase (0.05 mg/ml), oligonucleotide templates (1 µM), each NTP (4 mM), and $MgCl_2$ (25 mM), which supplies $Mg^{2+}$, a co-factor for the polymerase. This mixture is incubated at 37° C. and pH 8.1 (in for example 10 mM Tris-HCl buffer) for several hours (Milligan J. & Uhlenbeck O., 1989, Methods Enzymol (180) 51-62). Kits comprising the aforementioned components are commercially available such as the MEGA shortscript™ T7 kit (Ambion).

Purification protocols to obtain the oligoribonucleotide products from either of the above mentioned methods are generally known in the art and comprise amongst others gel electrophoresis, size exclusion chromatography, capillary electrophoresis and HPLC. Gel electrophorese is typically used to purify the full-length transcripts from the reaction mixture, but this technique is not amendable to production at larger scale. In a preferred embodiment of the present invention the purification means to obtain the oligoribonucleotide products consists of size exclusion chromatography, such as Sephadex G-25 resin, optionally combined with a phenol:chloroform:isoamyl extraction and ethanol precipitation.

It is a third object of the present invention to provide kits to perform the methods according to the invention. In one embodiment the kit comprises one or more of the following components a) instructions to design target-specific sense and antisense oligonucleotide templates; b) a chain extending enzyme; c) transcriptionbuffers; d) the nucleoside triphosphates (NTPs) for the four required ribonucleotide bases; e) purification means to obtain the sense and antisense oligoribonucleotide products. In a preferred embodiment of the present invention the chain-extending enzyme provided in the kit consists of an RNA polymerase, preferably an RNA polymerase selected from the group consisting of T7 RNA polymerase, T3 RNA polymerase and SP6 RNA polymerase. Even more preferably the chain extending enzyme provided in a kit according to the invention consist of T7 RNA polymerase.

The separating means provided in a kit according to the invention generally refers to purification protocols known in the art to obtain oligoribonucleotide products from a reaction mixture and comprise amongst others gel electrophoresis, size exclusion chromatography, capillary electrophoresis and HPLC. In a preferred embodiment of the present invention the purification means provided in a kit according to the invention consists of size exclusion chromatography columns or resins, such as Sephadex G-25 resin.

The instructions to design target-specific sense and antisense oligonucleotide templates should contemplate the method exemplified in FIG. 1 of the present invention. In essence the method comprises the following steps;

1) look for a target-specific sequence located within the coding sequence of the target gene and having the following sequence 5'-xx($n_{12-30}$)yy-3'. Wherein, x refers to the nucleotides transcribed from the promoter, y refers to the nucleotides complementary to the nucleotides transcribed form the promoter sequence, and $n_{12-30}$ refers to any oligonucleotide of 12 to 30 nucleotides 2) design a sense oligonucleotide template comprising the double stranded RNA polymerase promoter sequence according to the invention extended at the 5'end of the template strand with the complement oligonucleotide sequence of the target-specific sequence located in step 1), optionally extended with two additional nucleotides.

3) design an antisense oligonucleotide template comprising the double stranded RNA polymerase promoter sequence according to the invention extended at the 5'end of the template strand with the reverse oligonucleotide sequence of the target-specific sequence located in step 1), optionally extended with two additional nucleotides.

In a preferred embodiment the methods of the present invention use T7 RNA polymerase as chain extending enzyme. In said embodiment the method to design target-specific sense and antisense oligonucleotide templates would comprise the following steps;

1) look for a target-specific sequence located within the coding sequence of the target gene and having the following sequence 5'-gg($n_{12-30}$)cc-3' (SEQ ID NO: 47);

2) design a sense oligonucleotide template having the following sequence 5' TAATACGACTCACTATAGG (SEQ ID NO: 48)

3' ATTATGCTGAGTGATATcc (n complement)$_{12-30}$ gg (SEQ ID NO: 49)—optionally extended with two additional nucleotides, wherein (n complement)$_{12-30}$ refers to the complement oligonucleotide sequence of the target-specific sequence located in step 1); and 3) design an antisense oligonucleotide template having the following sequence 5' TAATACGACTCACTATAGG (SEQ ID NO: 48) 3' ATTATGCTGAGTGATATcc (n reverse)$_{12-30}$ gg (SEQ ID NO: 50)—optionally extended with two additional nucleotides, wherein (n reverse)$_{12-30}$ refers to the reverse oligonucleotide sequence of the target-specific sequence located in step 1).

In a specific embodiment the methods of the present invention are used for the synthesis of small interfering RNAs (siRNAs). In said embodiment the method to design target-specific sense and antisense siRNA templates would comprise the following steps;

1) look for a target-specific sequence located within the coding sequence of the target gene and having the following sequence 5'-xx($n_{15-30}$)yy-3'. Wherein, x refers to the nucleotides transcribed from the promoter, y refers to the nucleotides complementary to the nucleotides transcribed form the promoter sequence, and $n_{15-30}$ refers to any oligonucleotide of 15 to 30 nucleotides;

2) design a sense oligonucleotide siRNA template comprising the double stranded RNA polymerase promoter sequence according to the invention extended at the 5'end of the template strand with the complement oligonucleotide sequence of the target-specific sequence located in step 1), extended with two additional nucleotides, preferably two adenine residues;

3) design an antisense oligonucleotide siRNA template comprising the double stranded RNA polymerase promoter sequence according to the invention extended at the 5'end of the template strand with the reverse oligonucleotide sequence of the target-specific sequence located in step 1), extended with two additional nucleotides, preferably two adenine residues.

In the specific embodiment, where the methods to synthesize siRNAs make use of T7 RNA polymerase as chain extending enzyme, the method to design target-specific sense and antisense siRNA templates would comprise the following steps;

1) look for a target-specific sequence located within the coding sequence of the target gene and having the following sequence 5'-gg($n_{15-30}$)cc-3' SEQ ID NO: 51);

2) design a sense oligonucleotide siRNA template having the following sequence 5' TAATACGACTCACTATAGG (SEQ ID NO: 52)

3' ATTATGCTGAGTGATATcc (n complement)$_{15-30}$ gg aa (SEQ ID NO: 53)

wherein (n complement)$_{15-30}$ refers to the complement oligonucleotide sequence of the target-specific sequence located in step 1); and 3) design an antisense oligonucleotide siRNA template having the following sequence 5' TAATACGACTCACTATAGG (SEQ ID NO: 52)

3' ATTATGCTGAGTGATATcc (n reverse)$_{15-30}$ gg aa (SEQ ID NO: 54)

wherein (n reverse)$_{15-30}$ refers to the reverse oligonucleotide sequence of the target-specific sequence located in step 1).

Accordingly, the present invention provides a kit for the synthesis of short double stranded target-specific RNAs the kit comprising at least one of the following components; a) instructions to design target-specific sense and antisense oligonucleotide templates; b) a chain extending enzyme; c) transcriptionbuffers; d) the nucleoside triphosphates (NTPs) for the four required ribonucleotide bases; e) purification means to obtain the sense and antisense oligoribonucleotide products.

Thus in a further embodiment the present invention provides kits for the synthesis of small interfering RNAs the kit comprising at least one of the following components; a) instructions to design target-specific sense and antisense siRNA templates; b) a chain extending enzyme; c) transcriptionbuffers; d) the nucleoside triphosphates (NTPs) for the four required ribonucleotide bases; e) purification means to obtain the sense and antisense oligoribonucleotide products.

It is also an object of the present invention to provide the means for any of the disclosed methods for the in vitro synthesis of short double stranded RNAs. Accordingly the present invention provides;

i) a method to design target-specific sense and antisense oligonucleotide templates ii) a chain extending enzyme according to the invention for use in a method for the in vitro synthesis of short double stranded RNAs iii) purification means to obtain the sense and antisense oligoribonucleotide products.

iv) reagents for the reaction mixture such that the sense and antisense oligoribonucleotide products are formed from the target-specific sense and antisense oligonucleotide templates using a chain extending enzyme according to the invention It is a further object of the present invention to use the siRNAs obtainable by a method of the present invention in a process for inhibiting expression of a target gene in a cell. The process comprising introduction of siRNAs obtainable by a method of the present invention, into a cell.

The target gene may be a gene derived from the cell (i.e., a cellular gene), an endogenous gene (i.e., a cellular gene present in the genome), a transgene (i.e., a gene construct inserted at an ectopic site in the genome of the cell), or a gene from a pathogen which is capable of infecting an organism from which the cell is derived. Depending on the particular target gene and the dose of double stranded RNA material delivered, this process may provide partial or complete loss of function for the target gene.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. The cell having the target gene may be from the germ line or somatic, totipotent or pluripotent, dividing or non-dividing, parenchyma or epithelium, immortalized or trans- formed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

The isolated RNA obtainable by a method of the present invention consists of target-specific short double stranded RNAs, wherein said target-specific short double stranded RNAs are less than 50 nucleotides, preferably less than 30 nucleotides long, even more preferably 30-12 nucleotides, characterized by comprising at the 5'end nucleotides transcribed from the promoter sequence and at the 3'end nucleotides complementary to the nucleotides transcribed from the promoter sequence, preferably the number of nucleotides transcribed from the promoter sequence and the number of nucleotides complementary to the nucleotides transcribed from the promoter sequence consist of 2, 3, or 4 nucleotides, more preferably of 2 nucleotides.

The short double stranded RNAs obtainable by a method of the present invention are optionally extended at the 3'end with 2 or 3 additional nucleotides and could in a further embodiment of the present invention being represented as having the following sense sequence 5'-xx($n_{12-30}$)yy-3' wherein x refers to the nucleotides transcribed from the promoter sequence, y refers to the nucleotides complementary to the nucleotides transcribed form the promoter sequence, and $n_{12-30}$ refers to any oligonucleotide of 12 to 30 nucleotides. In a specific embodiment the short double stranded RNAs have as sense sequence 5'-gg($n_{15-30}$)cc-3' (SEQ ID NO: 51) wherein g refers to the nucleotide guanosine transcribed from the truncated T7 RNA polymerase promoter sequence (as shown in FIG. 1), c refers to the nucleotide cytosine complementary to the nucleotides transcribed form the truncated T7 RNA polymerase promoter (as shown in FIG. 1) sequence, and $n_{15-30}$ refers to any oligonucleotide of 15 to 30 nucleotides.

The RNA may be directly introduced into the cell (i.e., intracellularly); or introduced extracellularly into a cavity, interstitial space, into the circulation of an organism, introduced orally, or may be introduced by bathing an organism in a solution containing the RNA. Methods for oral introduction include direct mixing of the RNA with food of the organism, as well as engineered approaches in which a species that is used as food is engineered to express the RNA, then fed to the organism to be affected. For example, the RNA may be sprayed onto a plant or a plant may be genetically engineered to express the RNA in an amount sufficient to kill some or all of a pathogen known to infect the plant.

Physical methods of introducing nucleic acids, for example, injection directly into the cell or extracellular injection into the organism, may also be used. We disclose herein that in HeLa cells, double-stranded RNA introduced outside the cell inhibits gene expression.

Vascular or extravascular circulation, the blood or lymph system, the phloem, the roots, and the cerebrospinal fluid are sites where the RNA may be introduced. A transgenic organism that expresses RNA from a recombinant construct may be produced by introducing the construct into a zygote, an embryonic stem cell, or another multipotent cell derived from the appropriate organism.

Physical methods of introducing nucleic acids include injection of a solution containing the RNA, bombardment by particles covered by the RNA, soaking the cell or organism in a solution of the RNA or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or otherwise increase inhibition of the target gene.

The present invention may be used to introduce RNA into a cell for the treatment or prevention of disease. For example, dsRNA may be introduced into a cancerous cell or tumor and thereby inhibit gene expression of a gene required for maintenance of the carcinogenic/tumorigenic phenotype. To prevent a disease or other pathology, a target gene may be selected which is required for initiation or maintenance of the disease/pathology. Accordingly, in a further embodiment the invention provides a pharmaceutical composition comprising short double stranded RNAs obtainable by a method of the present invention to inhibit gene expression of a target gene and an appropriate carrier. The composition may be administered in any suitable way, e.g. by injection, by oral, intra-ocular, topical, nasal, rectal application etc. The carrier may by any suitable pharmaceutical carrier, preferably, a carrier is used, which is capable of increasing the efficacy of the RNA molecules to enter the target cells, for example liposomes, natural viral capsids or by chemically or enzymatically produced artificial capsids or structures derived therefrom.

Another utility of the present invention could be a method of identifying gene function in an organism comprising the use of double-stranded RNA to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceutics, understanding normal and pathological events associated with development, determining signaling pathways responsible for postnatal development/aging, and the like. The increasing speed of acquiring nucleo-tide sequence information from genomic and expressed gene sources, including total sequences for the human, mouse, yeast, *D. melanogaster*, and *C. elegans* genomes, can be coupled with the invention to determine gene function in an organism (e.g., nematode). The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

A simple assay would be to inhibit gene expression according to the partial sequence available from an expressed sequence tag (EST). Functional alterations in growth, development, metabolism, disease resistance, or other biological processes would be indicative of the normal role of the EST's gene product.

It is thus an object of the present invention to provide a method to inhibit expression of a target gene in a cell comprising introduction of RNA into a cell wherein said RNA comprises target-specific short double stranded RNA, wherein said target-specific short double stranded RNA is less than 50 nucleotides, preferably less than 30 nucleotides long, even more preferably 30-12 nucleotides long, characterized by comprising at the 5'end nucleotides transcribed from the promoter sequence and at the 3'end nucleotides complementary to the nucleotides transcribed from the promoter sequence wherein said promoter sequence is being recognized by an RNA polymerase. In a further embodiment the promoter sequence is being recognized by an RNA polymerase selected from the group consisting of T7 RNA polymerase, T3 RNA polymerase or SP6 RNA polymerase.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLE 1

EGFP and GL3 Specific short dsRNAs Transcribed in Vitro, induce RNA Interference in Human Cells Materials and Methods Plasmid Constructs Luciferase+ was expressed from the plasmid pGL3-control (Promega). EGFP was expressed from EGFP/pcDNA5-FRT, which contains the EGFP gene from pEGFP (Clontech) directionally ligated into the HindIII and NotI sites of the mammalian expression vector pcDNA5/FRT (Invitrogen).

In Vitro Transcription and Hybridization of siRNAs

Oligo template strands were hybridized to a sense T7 promoter sequence (5'TAATACGACTCACTATAGG) (SEQ ID NO: 55) in 10 mM Tris-HCl pH 9.0, 100 mM NaCl, 1 mM EDTA by boiling for 2' and cooling slowly to room temperature over 2-3 hr. Transcription was performed using the MEGAshortscript™ T7 kit (Ambion) according to the manufacturer's instructions. siRNA strands were purified over G-25 spin columns, phenol:chloroform:isoamyl alcohol (25: 24:1) extracted using Heavy Phase-Lock Gels (Eppendorf), and ethanol precipitated overnight at −80° C. Complementary siRNA strands were hybridized in 1 mM Tris-HCl pH 8.0, 1 mM EDTA pH 8.0 by boiling for 2' and cooling slowly to room temperature over 2-3 hr. Hybridization was assessed by running the ds- and ss-siRNAs on non-denaturing 20% polyacrylamide TBE gels.

Cell Lines and Transfection

HeLa cells were grown in DMEM with high glucose and 1-glutamine (Invitrogen) supplemented with 1.8 mM 1-glutamine, 9% FBS, and 45 U/l pen/strep. Cells were transfected in a manner similar to that described in Elbashir et al. (2001). 24 hr before transfection, cells were trypsinized and diluted with growth medium lacking antibiotics to $3\times10^5$ cells/ml. 0.5 ml of cells were seeded into each well of a 24-well plate. The cells were transfected with 1 µg of GL3-control or EGFP/pcDNA5-FRT reporter constructs and 50 pmol of single-stranded or 25 pmol double-stranded siRNAs, except where otherwise noted, using Lipofectamine™ 2000 (LF2000; Invitrogen) according to the manufacturer's instructions. Specifically, we used 21 µl of LF2000 per well in 48 µl of serum-free medium lacking antibiotics. The diluted LF2000 was pre-incubated at room temperature for 1' prior to mixing with reporter and/or siRNAs diluted in the same medium to 50 µl total volume. Complexes were then incubated at room temperature for 20' before being added to the cells. EGFP and GL3 reporter gene assays were performed after 24 hrs. For the JNK2α1 siRNA experiment and GL3 siRNA dose response experiment, 6-well plates were used. Cell numbers were increased 4-fold and reagent amounts 5-fold. For the JNK2α1 siRNA experiment, cells were harvested for RNA isolation and protein extraction were approximately 48 hr post-transfection.

Reporter Gene Assays

FACS analysis of EGFP-transfected cells was performed using a FACScan (Beckton-Dickinson). Cells were trypsinized and washed with PBS prior to resuspension in FACS fixing solution (PBS+1% formaldehyde). Transfection efficiencies were estimated by comparing samples transfected with water with those transfected with EGFP/pcDNA5-FRT and were typically 75-90%. The extent of RNAi induced by transcribed or synthetic siRNAs was estimated from the change in the mean GFP fluorescence in samples with or without cotransfected siRNAs.

For luciferase assays, cells were trypsinized and 100 µl aliquots were transferred to triplicate wells in white 96-well tissue culture plates. Assays were performed using the Luc-Screen™ System (Applied Biosystems) and a TopCount-NXT™ Microplate Scintillation and Luminescence Counter (Packard) according to the manufacturers' instructions.

Northern and Western Blotting

Total RNA was prepared from samples of approximately $10^6$ HeLa cells using the RNeasy Mini Kit (Qiagen) according to the manufacturer's instructions. Samples were run on pre-cast MOPS Latitude RNA agarose gels (BioWhittaker Molecular Applications) and transferred to Hybond-XL nylon membranes (AP Biotech) according to the manufacturers' instructions. DNA probes were made using the Rediprime II system (AP Biotech) according to the manufacturer's instructions. Hybridization was performed in Rapid-Hyb solution (AP Biotech) according to the manufacturer's instructions.

Nuclear and cytoplasmic protein extracts were made by the method described in Gordon (1991), substituting Complete Protease Inhibitor Cocktail (Roche) for leupeptin, aprotinin, and pepstatin and omitting sodium deoxycholate.

Extracts were run on 4-20% SDS polyacrylamide minigels (Invitrogen) with Rainbow protein marker (AP Biotech) and electroblotted onto 0.2 µm Transblot nitrocellulose membranes (BioRad). The blots were rinsed in PBS+0.05% Tween-20 and incubated overnight at 4° C. with 1:150 diluted JNK2 D2 mouse monoclonal antibody (Santa Cruz Biotech) in PBS/Tween-20 with 5% milk powder. The blots were then washed three times in PBS/Tween-20 before a 45 min incubation with 1:3000 HRP-conjugated goat anti-mouse antibodies (BioRad). Three more washes and a 30 min incubation in PBS/Tween-20 were performed before detection by the ECL system (AP Biotech).

Results

RNAi has been previously demonstrated using siRNAs that are double-stranded except for two 3' overhanging nucleotides (Elbashir et al. 2001; Caplen et al. 2001). In order to relatively quickly and inexpensively create a variety of siRNAs for multiple cellular targets, we designed a scheme to generate the molecules using in vitro transcription techniques.

Milligan et al. (1987) describe the use of partially single-stranded DNA oligo templates for transcription by T7 DNA polymerase. The standard T7 minimal promoter includes three guanosine nucleotides at the 3' end which are incorporated as the first three bases of the transcript. However, the third guanosine can usually be replaced with other nucleotides without significant reduction of in vitro transcription yields (Milligan et al. 1987). Therefore, siRNAs produced by this method should include two 5' guanosine nucleotides. Two complementary cytosine nucleotides are needed near the 3' end of each siRNA strand to base pair with the 5' guanosines on the other strand. siRNAs of a given length produced in this manner should be able to target sequences appearing approximate once every 250 nucleotides on average in an mRNA.

We designed DNA oligo templates with the constraints above in mind (FIG. 1). Each template is used to transcribe one strand of an siRNA. The strands are crudely purified by passage over a Sephadex G-25 size exclusion column, phenol:chloroform extraction, and ethanol precipitation. The strands are then resuspended in annealing buffer and hybridized by boiling and slow cooling.

Figure 2C:
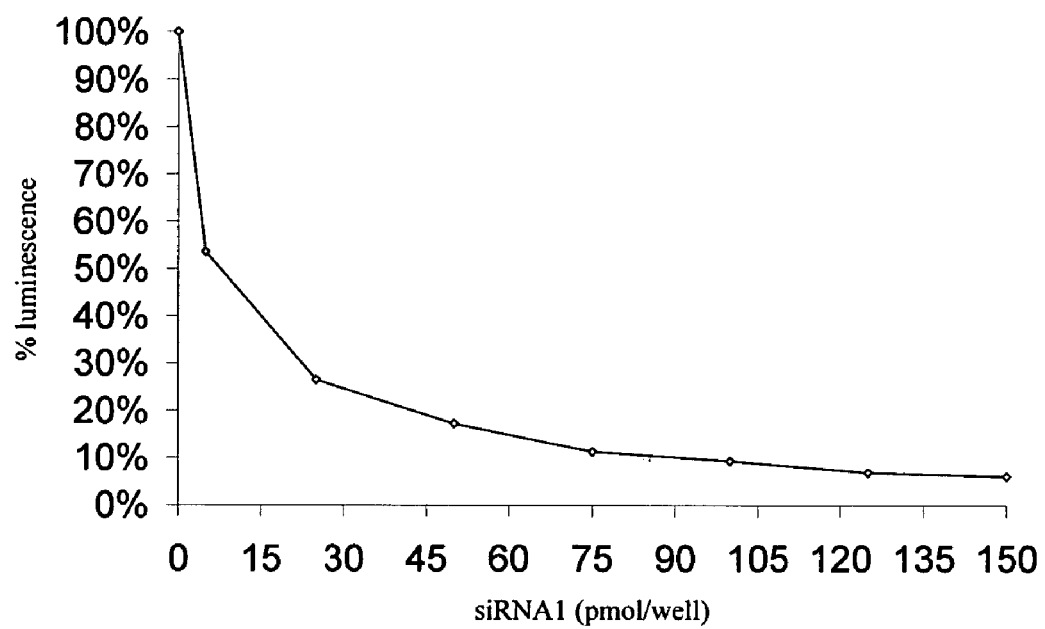
FIG. 2C: Dose response curve of the GL3-siRNA 1 inhibitory effect on luciferase expression in pGL3-control transfected HeLa cells.
Figures 3A, 3B:
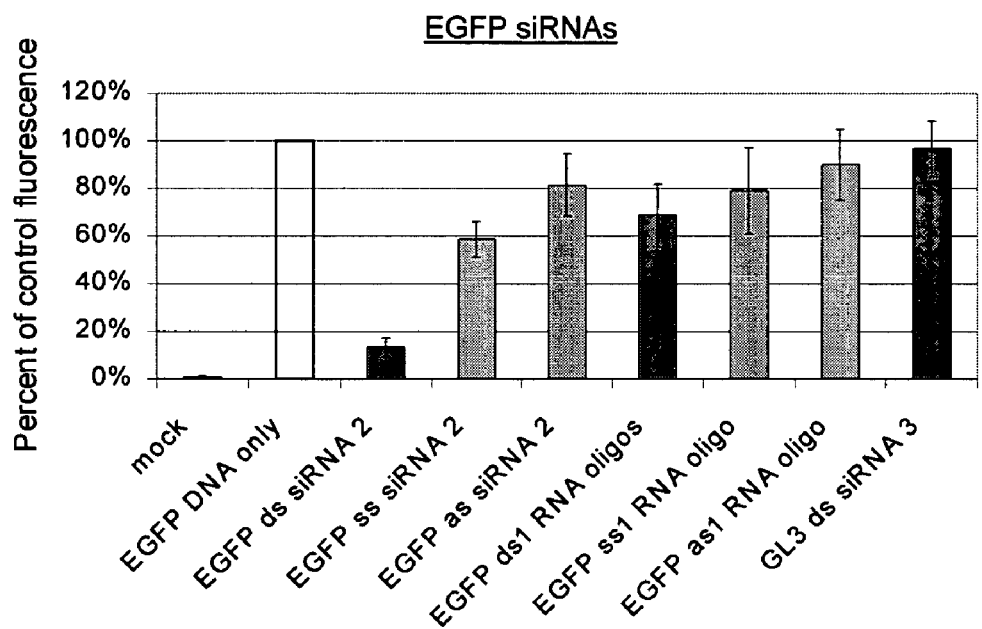
FIG. 3A: EGFP target-specific double stranded siRNAs used in a FACS analysis of EGFP-transfected HeLa cells. EGFP ds siRNA 2 was made using the in vitro method of the invention. EGFP ds siRNA oligo was chemically synthesized (Vargeese, C. et al., 1988, Nucleic Acid Res. (26), 1046-1050) Figure discloses SEQ ID NOS: 29-32, respectively, in order of appearance.
FIG. 3B: Effects of EGFP target-specific siRNAs and of EGFP antisense single stranded siRNAs on GFP fluorescence in EGFP-transfected HeLa cells using FACScan analysis (Beckton-Dickinson). Cells transfected with EGFP DNA only were taken as 100%.

Our in vitro transcribed siRNAs differ from the chemically synthesized variety used previously in two ways. First, all other reported siRNAs have been highly purified. Second, in vitro transcribed siRNAs retain a 5' triphosphate group. Like the siRNA species produced in vivo as part of the natural RNAi mechanism, chemically synthesized RNA oligonucleotides used to make siRNAs have carried 5' monophosphates. In order to determine if these differences render our siRNAs incompetent to induce RNAi, we first tested double-stranded siRNAs designed to target two reporter genes—EGFP and GL3 (FIGS. 2 and 3). Mean results and standard errors from at least three independent experiments are shown (FIG. 2B, FIG. 3B).

The transcribed GL3 ds siRNA 1 reduced luciferase activity from the cotransfected pGL3-control reporter plasmid by approximately 5-fold while the antisense strand alone in double-molar concentration had no effect. A similar result was observed with a chemically synthesized GL3 ds siRNA (ds1 RNA oligos). The second transcribed siRNA had a more modest effect. While the third transcribed siRNA had a strong effect, significant activity was also seen from the antisense strand alone. The strength of the effect from the double-stranded species is dose dependent (FIG. 2C) and modifies steady-state RNA levels. EGFP ds siRNA 2 also had a modest effect on luciferase activity (FIG. 2B). However, this effect appears to be non-specific and shows a limited response at increasing doses.

The same transcribed EGFP ds siRNA 2 strongly reduced GFP fluorescence in cells cotransfected with the EGFP/pcDNA5-FRT reporter (FIG. 3B). Much more modest effects were evident from sense or antisense strands alone or from a chemically synthesized siRNA (EGFP ds1 RNA oligos) or its component parts. GFP fluorescence was not affected by the non-specific GL3 ds siRNA 3.

The above mentioned in vitro transcribed (IVT) luciferase ds siRNAs yielded inhibition of luciferase activity to a different extent. As a positive control for RNAi activity, we used a chemically synthesized luciferase ds siRNA. In our hands, luciferase activity from the cotransfected pGL3-control reporter plasmid was reduced approximately 5-fold by the synthetic ds siRNAs. Transfection efficiencies for all experiments varied between 91 and 95%. One IVT-luciferase ds siRNA (GL3 ds siRNA 1) reduced luciferase activity 78%, while the antisense RNA strand alone at twice the molar concentration of the ds siRNA had no effect. The second IVT-siRNA (GL3 ds siRNA 2) we tested had a more modest effect (36% inhibition). While the third IVT-siRNA had a strong effect (82% inhibition), significant activity was also seen from the antisense RNA strand alone (55% inhibition), confounding the result. A mixture of the three IVT-siRNAs, each at one-third the molar concentration used for them individually, had an intermediate effect (70% inhibition) rather than a synergistic one, suggesting that there may be no advantage to using multiple siRNAs to target the same gene. We could show the inhibitory effect from the ds species to be dose-dependent. While a non-specific GFP siRNA (GFP ds siRNA 2) also had a modest effect (46% inhibition) on luciferase activity, this appears to be non-specific and shows a limited response at increasing doses (data not shown).

The same IVT-GFP ds siRNA (GFP ds siRNA 2) strongly reduced GFP fluorescence in cells cotransfected with the GFP/pcDNA5-FRT reporter (87% inhibition). Much more modest effects were evident from sense (41%) or antisense (19%) strands alone or from a chemically synthesized siRNA (GFP ds1 RNA oligo) or its component parts. GFP fluorescence was, as expected, not affected by the non-specific luciferase ds siRNA 3.

To demonstrate that endogenous gene expression can also be affected by transcribed siRNAs, we targeted the products of the JNK2α1 (FIG. 4A) and CDS-1 (FIG. 4B) genes. Western and Northern blot analysis revealed specific reduction of JNK2α1 protein and RNA levels in samples in nuclear extracts of HeLa cells transfected with either a transcribed siRNA (JNK2α1 ds siRNA 1—estimated 87% reduction) or a chemically synthesized siRNA (JNK2α1 ds1 RNA oligos—estimated 76% reduction) when compared to cells transfected with water (mock), EGFP/pcDNA5-FRT plasmid as a transfection control (EGFP DNA only), single strands of siRNAs, or a non-specific siRNA (EGFP ds siRNA 2).

Western blot analysis revealed modest (up to 67%) reduction of CDS 1 protein levels in cytoplasmatic extracts of HeLa cells transfected with CDS 1-specific IVT-siRNAs (FIG. 4) but not in cells transfected with an unspecific siRNA when compared to mock-transfected cells.

EXAMPLE 2

Mouse Insr Specific short dsRNAs Transcribed in Vitro, Knockdown Insr in Liver of Balb/C Mice Male Balb/C mice (approx 25 g) (standard housing, free access to chow/water) received a tail vein injection of either saline, 2.3 ml, or saline containing 40 micrograms of siRNA directed against the murine insulin receptor (NCBI accession number NM_010568; bases 2536-2556) prepared,by the truncated T7 promoter method of in vitro transcription, along with 800 U RNase inhibitor.

The injections were administered as rapidly as possible (8-10 seconds). Two control and two siRNA treated mice were sacrificed at 24, at 48 and at 72 hours; the liver was quickly removed,weighed, and frozen in dry ice/isopropanol. Total RNA was extracted using pulverized frozen tissue and RNEasy Maxi kits (Qiagen).

After first strand cDNA synthesis, mRNA for the insulin receptor was assayed by Q-PCR using the Smart Cycler (primers: F 3526-3548, R 3744-3768) and results were normalized to cyclophilin A expression also by Q-PCR (bases 157-182 and 496-521 of NCBI accession number NM_017101).

The invention claimed is:

1. A method for the synthesis of target-specific short double stranded RNAs of less than 30 nucleotide long comprising the steps of:
   a) combining a target-specific sense oligonucleotide template and a T7 RNA polymerase in a reaction mixture such that a template extended, sense oligoribonucleotide, product is formed;
   b) combining a target-specific antisense oligonucleotide template and T7 RNA polymerase in a reaction mixture such that a template extended, antisense oligoribonucleotide, product is formed; and
   c) hybridizing the sense oligoribonucleotide product obtained in step a) with the complementary antisense oligoribonucleotide product obtained in step b), characterized in that;
   the oligonucleotide templates of step a) and b) comprise an RNA polymerase promoter sequence consisting of the truncated T7 RNA polymerase promoter sequence as set forth in SEQ ID NO: 56, extended at the 5'-end of the template strand with the target-specific template sequence, wherein said target-specific template sequence comprises at the 5'-end two guanosine (g) nucleotides and at the 3'-end two cytosine (c) nucleotides, wherein said two cytosine nucleotides being the first two nucleotides of said promoter sequence.

2. A method for the synthesis of target-specific short double stranded RNAs of less than 30 nucleotide long comprising the steps of:
  a) combining a target-specific sense oligonucleotide template and a T7 RNA polymerase in a reaction mixture such that a template extended, sense oligoribonucleotide, product is formed;
  b) combining a target-specific antisense oligonucleotide template and T7 RNA polymerase in a reaction mixture such that a template extended, antisense oligoribonucleotide, product is formed; and
  c) hybridizing the sense oligoribonucleotide product obtained in step a) with the complementary antisense oligoribonucleotide product obtained in step b), characterized in that;
  wherein the oligonucleotide templates of step a) and b) are characterized by being partially double stranded DNA oligo templates comprising a double stranded RNA polymerase promoter sequence consisting of the truncated T7 RNA polymerase promoter sequence as set forth in SEQ ID NO: 56, extended at the 5'-end of the template strand with the target-specific template sequence, wherein said target-specific template sequence comprises at the 5'-end two guanosine (g) nucleotides and at the 3'-end two cytosine (c) nucleotides, wherein said two cytosine nucleotides being the first two nucleotides of said promoter sequence.

3. A method for the synthesis of small interfering RNAs (siRNAs) of 12-30 nucleotides comprising the steps of;
  a) combining a sense siRNA template with T7 RNA polymerase in a reaction mixture such that a template extended sense oligoribonucleotide product is formed;
  b) combining an antisense siRNA template with T7 RNA polymerase in a reaction mixture such that a template extended antisense oligoribonucleotide product is formed; and
  c) hybridizing the sense oligoribonucleotide product obtained in step a) with the antisense oligoribonucleotide product obtained in step b);
  whereby the siRNA templates of step a) and b) comprise a double stranded RNA polymerase promoter sequence consisting of the truncated T7 RNA polymerase sequence as set forth in SEQ ID NO: 56, extended at the 5'-end of the template strand with the target-specific template sequence as defined in claim 1, wherein the template further contains 2 or 3 additional nucleotides.

* * * * *

UNITED STATES PATENT AND TRADEMARK OFFICE
CERTIFICATE OF CORRECTION

| | | |
|---|---|---|
| PATENT NO. | : 7,659,391 B2 | Page 1 of 1 |
| APPLICATION NO. | : 10/494663 | |
| DATED | : February 9, 2010 | |
| INVENTOR(S) | : De Backer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 976 days.

Signed and Sealed this

Thirtieth Day of November, 2010

David J. Kappos
*Director of the United States Patent and Trademark Office*

SEQUENCE LISTING

<160> NUMBER OF SEQ ID NOS: 56

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggaucaugaa agaaugucc                                              19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taatacgact cactatagg                                                  19

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaggacattc tttcatgatc ctatagtgag tcgtatta                             38

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taatacgact cactatagg                                                  19

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaggatcatg aaagaatgtc ctatagtgag tcgtatta                             38

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcuaugaag agauacgcc                                                  19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gggcauuucg cagccuacc                                                  19

-continued

```
<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ggugccaacc cuauucucc                                                    19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cuuacgcuga guacuucga                                                    19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gggcgaggag cguucacc                                                     19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ccaccggcaa gcugcccgu                                                    19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggaucaugaa agaaugucc                                                    19

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gguguuguaa aagaucagcc                                                   20

<210> SEQ ID NO 14
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ccaagggauu guuugugcu                                                       19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggcagcguua cccagucccc                                                      19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ggcuccuccu cacagucccc                                                      19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ggagccuacc ccugccccc                                                       19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggaaaggaaa acgccgucc                                                       19

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggaucaugaa agaauguccu u                                                    21

<210> SEQ ID NO 20
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ggacauucuu ucaugauccu u                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggcuaugaag agauacgccu u                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcguaucuc uucauagccu u                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gggcauuucg cagccuaccu u                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gguaggcugc gaaaugcccu u                                              21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ggugccaacc cuauucuccu u                                              21

<210> SEQ ID NO 26
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 26
ggagaauagg guuggcaccu u                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
cuuacgcuga guacuucgat t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
ucgaaguacu cagcguaagt t                                              21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gggcgaggag cuguucaccu u                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ggugaacagc uccucgcccu u                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 31
ccaccggcaa gcugcccgut t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
acgggcagcu ugccgguggt t                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ggaucaugaa agaauguccu u                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ggacauucuu ucaugauccu u                                              21

<210> SEQ ID NO 35
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gguguuguaa aagaucagcc uu                                             22

<210> SEQ ID NO 36
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ggcugaucuu uuacaacacc uu                                             22

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
```

-continued

```
      Synthetic oligonucleotide
<220> FEATURE:
<223> OTHER INFORMATION: Description of Artificial Sequence: Synthetic
      oligonucleotide

<400> SEQUENCE: 37
ccaagggauu guuugugcut t                                                   21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
agcacaaaca aucccuuggt t                                                   21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ggcagcguua cccagucccu u                                                   21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gggacugggu aacgcugccu u                                                   21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcuccuccu cacagucccu u                                                   21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gggacuguga ggaggagccu u                                                   21

<210> SEQ ID NO 43
```

-continued

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ggagccuacc ccugccccu u                                                    21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gggggcaggg guaggcuccu u                                                   21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ggaaaggaaa acgccguccu u                                                   21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ggacggcguu uuccuuuccu u                                                   21

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, g, t, unknown or other and this region
      may encompass 12-30 bases

<400> SEQUENCE: 47
ggnnnnnnnn nnnnnnnnnn nnnnnnnnnn nncc                                     34

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
```

```
taatacgact cactatagg                                              19
```

<210> SEQ ID NO 49
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, g, t, unknown or other and this region
      may encompass 12-30 bases that correspond to
      the complement oligonucleotide sequence of the
      target-specific sequence

<400> SEQUENCE: 49

```
ggnnnnnnnn nnnnnnnnnn nnnnnnnnnn nncctatagt gagtcgtatt a          51
```

<210> SEQ ID NO 50
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, g, t, unknown or other and this region
      may encompass 12-30 bases that correspond to
      the reverse oligonucleotide sequence of the
      target-specific sequence

<400> SEQUENCE: 50

```
ggnnnnnnnn nnnnnnnnnn nnnnnnnnnn nncctatagt gagtcgtatt a          51
```

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, g, t, unknown or other and this region
      may encompass 15-30 bases

<400> SEQUENCE: 51

```
ggnnnnnnnn nnnnnnnnnn nnnnnnnnnn nncc                             34
```

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

```
taatacgact cactatagg                                              19
```

<210> SEQ ID NO 53
<211> LENGTH: 53
<212> TYPE: DNA
<213> ORGANISM: Artificial Sequence
<220> FEATURE:

-continued

```
<223> OTHER INFORMATION: Description of Artificial Sequence: Synthetic
      oligonucleotide
<220> FEATURE:
<221> NAME/KEY: modified_base
<222> LOCATION: (5)..(34)
<223> OTHER INFORMATION: a, c, g, t, unknown or other and this region
      may encompass 15-30 bases that correspond to
      the complement oligonucleotide sequence of the
      target-specific sequence

<400> SEQUENCE: 53
aaggnnnnnn nnnnnnnnnn nnnnnnnnnn nnnncctata gtgagtcgta tta        53

<210> SEQ ID NO 54
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(34)
<223> OTHER INFORMATION: a, c, g, t, unknown or other and this region
      may encompass 15-30 bases that correspond to
      the reverse oligonucleotide sequence of the
      target-specific sequence

<400> SEQUENCE: 54
aaggnnnnnn nnnnnnnnnn nnnnnnnnnn nnnncctata gtgagtcgta tta        53

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
taatacgact cactatagg                                              19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cctatagtga gtcgtatta                                              19
```